United States Patent [19]

Andre et al.

[11] Patent Number: 5,165,935

[45] Date of Patent: Nov. 24, 1992

[54] COSMETIC OR DERMATOLOGICAL COMPOSITION, CONTAINING KOLA EXTRACTS AND METHOD FOR TREATMENT OF CELLULITIS

[75] Inventors: Patrice Andre, Neuville Aux Bois; Jocelyne Dominice, Olivet; Pierre Perrier, Orleans; Gérard Redziniak, St Cyr En Val, all of France

[73] Assignee: Parfums Christian Dior, Paris, France

[21] Appl. No.: 759,827

[22] Filed: Sep. 13, 1991

Related U.S. Application Data

[63] Continuation of Ser. No. 601,810, Oct. 31, 1990, abandoned.

[30] Foreign Application Priority Data

May 10, 1988 [FR] France ................................ 88 06306

[51] Int. Cl.$^5$ ........................ A61K 37/22; A61K 7/00
[52] U.S. Cl. .................................. 424/450; 424/195.1; 424/401; 514/860
[58] Field of Search ............... 424/195.1, 450; 428/402.2; 268/4.1, 4.3, 4.6

[56] References Cited

U.S. PATENT DOCUMENTS 4,684,522  8/1987  Marissal et al. .................. 424/195.1

FOREIGN PATENT DOCUMENTS 2092445  2/1982  United Kingdom ............. 424/195.1

Primary Examiner—Thurman K. Page
Assistant Examiner—Sally Gardner
Attorney, Agent, or Firm—Bryan Cave

[57] ABSTRACT

A cosmetic or dermatological composition comprising an extract of kola seeds substantially free of methylxanthine. Other embodiments include a composition comprising liposomes or hydrated lipidic lamellar phases containing an extract of kola seeds having a methylxanthine content or containing an extract of kola seeds substantially free of methylxanthine. Methods for treating cellulitis deposits present on body parts by application of the compositions of the present invention are also disclosed.

18 Claims, No Drawings

COSMETIC OR DERMATOLOGICAL COMPOSITION, CONTAINING KOLA EXTRACTS AND METHOD FOR TREATMENT OF CELLULITIS

This is a continuation of U.S. application Ser. No. 07/601,810 filed Oct. 31, 1990 now abandoned which is incorporated by reference herein.

The present invention relates essentially to a cosmetic or dermatological composition, in particular with slimming or anti-cellulitic action, containing kola extracts in free or liposomal form.

Quite an important number of cosmetic preparations for slenderizing certain superficial parts of the human body already exist on the market. They often contain products of natural origin, in particular vegetable origin, such as creeping ivy, caffeine, horse chestnut extracts, etc . . . The literature also gives a large number of slimming formulas, from which can be cited by way of examples, U.S. Pat. No. 4,525,359 to Greenway III et al., which proposes the use as active principle, of adrenergic beta-stimulants, preferably theophylline, isoproterenol, forskoline and epinephrine. Also before that, the U.S. Pat. No. 4,288,433 to Koulbanis et al., had recommended the use of methylxanthines, in particular caffeine, in the preparation of slimming products for localized application on the zones to be treated.

Yet up to now, none of the formulations put on the market for body slimming have been found truly efficient. This is the reason why it has quite often been recommended to use said formulations in combination with a slimming "program" or diet. This is particularly the case with U.S. Pat. No. 4,525,359, so that it is never absolutely certain, when slimming results are observed, whether these are due to the slimming program or diet, or to the slimming formulation.

The result is that a large number of active principles have been proposed for slimming by chemists or suppliers.

Particularly, French Patent No. 2 499 405 describes a slimming and anticellulitic cosmetic composition based on a plant extract containing saponins, an extract of Arnica Montana L. and an extract of Kola nut, as well as its preparation process.

Likewise, French Patent No. 2 554 344 describes a cosmetic composition with a slimming and anti-cellulitic action containing 0.5 to 10% by weight of a purine base of natural or synthetic origin, advantageously selected from extracts of coffee, tea, kola and mate, caffeine and theophylline, as well as derivatives thereof such as their salts and complexes; 0.5 to 10% by weight of an extract of Hedera Helix and 0.1 to 10% by weight of an extract of Ruscus aculeatus.

The Italian company Inverni Della Beffa similarly proposes extracts of Kola seeds which contain in particular, methylxanthines comprising caffeine, theobromine, theophylline, etc . . . and tannins, for their astringent, aromatizing and lipase-activating properties. Said company proposes two extracts in particular, namely dry kola extract, also called "extract 14" because of a titration of 14% of alcaloids expressed as caffeine the addition of which is recommended in the proportion of up to 1%.

The second extract is the fluid Lipa kola extract also called "Lipa extract" titrating less than 0.5% of alcaloids expressed as caffeine.

Given that the Lipa extract is virtually free of alcaloid, and that the slimming property was heretofore attributed to the methylxanthines, and in particular to caffeine, said Lipa extract is exclusively recommended for the preparation of astringent compositions in the proportion reaching up to 5%.

Intensive research conducted by the present inventors has revealed, completely unexpectedly, that the kola extracts containing substantially no methylxanthine, and in particular the said Lipa extract, were as active as the kola extract containing the methylxanthines, in particular the extract 14, on the lipolysis estimated from the type of adipocytes in culture.

Thus, the inventors working against the preconceived idea admitted in the art, relatively to the lack of activity or the inefficiency, in the treatment of cellulitis or of localized adiposis of products containing no methylxanthines, such as the Lipa extract containing substantially no methylxanthines, have discovered that the kola extracts containing substantially no methylxanthines, are at least as active as the kola extracts containing methylxanthines, such as extract 14.

Furthermore, and likewise completely unexpectedly, the present inventors, in studying the action of these two extracts, respectively extract 14 and extract Lipa, on the activity of adipocytes in culture, have discovered that these extracts, when they are encapsulated in liposomes, exhibit an activity which is definitely greater than that of the free extracts, namely the extracts not encapsulated in liposomes.

Thus, according to a first aspect, the present invention provides a cosmetic or dermatological composition, in particular with a slimming or anti-cellulitic action, characterized in that it comprises kola seed extracts containing substantially no methylxanthines; or hydrated, lipidic lamellar phases or liposomes containing total or partial extracts of kola seeds.

According to a special embodiment of the invention, the partial extracts of kola seeds are extracts containing substantially no methylxanthines, their methylxanthine content being less than about 0.5 per thousand, whereas the total extracts are dry extracts with a methylxanthine content of between about 10% and 14%.

According to another particular embodiment, the kola from which the extracts according to the invention are obtained is the Kola Nitida plant or the Cola Vera Shum plant.

The extraction processes usable according to the invention are processes known of anyone skilled in the art, utilizing for example organic solvents or mixtures of solvents, such as a hydro-alcoholic mixture.

It is for example possible to obtain total extracts of kola seeds according to the invention according to the process described in document FR-A-2 586 532, slightly modified as follows.

The kola seeds or nuts are ground and then subjected to an extraction treatment with a mixture of methanol:water or ethanol:water at 40–50%. The hydro-alcoholic extract is collected and then the alcohol is eliminated by evaporation.

The resulting aqueous solution is then dried by spraying or lyophilization, and then ground to obtain a stable total extract. Said total extract may be used as it is as total extract according to the invention.

According to another special embodiment of the invention, the kola seeds extracts according to the invention, containing substantially no methylxanthines, are obtained by any extraction process capable of substantially completely eliminating the methylxanthines.

It is then possible to prepare, according to the invention, from the aqueous solution obtained when implementing the above-described process, an extract containing substantially no methylxanthines, and in particular containing substantially no caffeine, by a treatment using a selective solvent of caffeine, such as a chlorinated solvent like dichloromethane, chloroform or trichloroethane, or another solvent on its own or in combination, as indicated in document U.S. Pat. No. 4,279,937 or EP-B-101 135, such as benzylic alcohol, methylethylketone or methyl acetate.

It is also possible to use the process described in document U.S. Pat. No. 4,279,937 of Procter, applicable to kola seeds, which uses a mixture of benzylic alcohol with another solvent, such as xylene, ethyl acetate, cyclopentane, cyclohexane.

According to a variant embodiment, the methylxanthines, and in particular caffeine, are alone extracted, at first, from kola seeds, said seeds being preferably ground beforehand. Then, the caffeine-free kola seeds are extracted according to a conventional process such as that described hereinabove for obtaining the total extract.

Several processes for extracting caffeine, hence methylxanthines are described in the literature. For example, the Journal of the Agricultural Chemical Society of Japan, (1985), 59, No. 9, pages 917-919, describes a selective process of extraction of caffeine using the hot water from intact tea leaves, which is directly usable for extracting the methulxanthines in water. This process, when applied to ground kola seeds, makes it possible to obtain caffeine-free kola seeds.

It is also possible to eliminate the methylxanthines with an extraction process using a gas in supercritic state, such as carbon dioxide, as described in the document Food Technology (Chicago) (1986), 40, No. 7, pages 57-64, as well as the document Journal of Food Sciences and Technology, (1986), 23, No. 6, pages 325-328.

In the compositions according to the invention, the proportions by weight of kola extracts, with respect to the total weight of the composition, can vary within wide limits. The preferred proportions are proportions by weight ranging between 0.01 and 10% by weight with respect to the total weight of the cosmetic and dermatological composition.

The incorporation of total or partial kola seed extracts in the hydrated lipidic lamellar phases or in the liposomes can be carried out according to any of the conventional methods. These are selected more particularly as a function of the more or less lipophilic or more or less hydrophilic nature of the extracts to be incorporated.

According to a preferred incorporation method, the preparation technique described in document EP-B1-0087 993 is used, optionally combined with a technique described in document EP-B1-0107 159.

Thus, it is for example possible to include the total or partial kola seed extracts in hydrated lipidic lamellar phases or in liposomes.

In the present description and claims, the word "lipidic" in the example "lipidic lamellar phase" covers all substances containing a so-called fatty carbon chain, generally higher than 5 carbon atoms, such substance being normally called "lipids".

According to the invention, the lipids used, in order to form either the above cited liposome, or the lipidic lamellar phases, are amphiphilic lipids, i.e. lipids constituted of molecules having a hydrophilic group which is indifferently ionic or non-ionic, and a lipophilic group, said amphiphilic lipids being capable of forming lipidic lamellar phases in the presence of an aqueous phase.

Particularly suitable lipids are: the phospholipids, the phosphoaminolipids, the glycolipids, the polyoxyethylene-based fatty alcohols, the optionally polyoxyethylene-based polyol esters. Such substances are, for example, constituted by a soya or egg lecithin, a phosphatidylserine, a sphyngomyelin, a cerebroside or an oxyethylene polyglycerol stearate. Said hydrated lipidic lamellar phases or the liposomes can be prepared as follows:

Step 1

An amphiphilic lipid, such as for example hydrogenated or non-hydrogenated soya lecithin, is dissolved in an organic solvent having a relatively low melting point, for example less than 100° C., at the atmospheric pressure, such as dichloromethane or methanol. It is also possible to dissolve a hydrophobic liquid such as a sterol like cholesterol or $\beta$-sitosterol, and advantageously an antioxidant such as $\alpha$-tocopherol.

In general, the quantity of hydrophobic lipids should not be higher by weight than 0.2 times the quantity of amphiphilic lipids.

Step 2

If the aim is to incorporate the total or partial kola seed extracts in the lipidic phase, then such extracts can be dissolved in the solution obtained in Step 1. In the case where a fraction of the extracts is not solubilized, said insoluble fraction is eliminated by filtration. The relative proportions of, on the one hand, lipids, and on the other hand, extracts, as active principles, can, for example range, by weight, between 8:2 and 9.9:0.1. Preferably, the mixture is stirred for 30 minutes at ordinary temperature.

Step 2 bis

In the case where the total or partial extracts of kola seeds are intended to be encapsulated in the aqueous phase inside the hydrated lipidic lamellar phases, instead of carrying out Step 2 above, said extracts will be dissolved in water and preferably in a suitable aqueous solution such as a buffer solution of "PBS phosphate buffer" type.

Step 3-A

The mixture obtained at the end of Step 1 or Step 2 is introduced in a rotary flask, and evaporated by heating in a water-bath, optionally under reduced pressure.

After evaporation of the organic solvent, the lipidic film which has formed on the walls is taken up under stirring with water or with a suitable aqueous solution such as a buffer solution of "PBS phosphate buffer" type.

When the mixture obtained directly in Step 1 is used, without passing by Step 2, the aqueous solution obtained at the end of Step 2 bis is used.

Preferably, the quantity of water or of aqueous solution is at least equal, by weight, to 8 times the quantity of lipids contained in the flask.

A suspension of liposomes is thus obtained, which can then be homogenized by any suitable means, such as for example ultrasonic means.

Step 3-B

A variant of the process for the preparation of the compositions according to the invention which contain the above cited extracts incorporated in hydrated lipidic lamellar phases or in liposomes, consists in using the process described in document EP-B1-0087 993, comprising spraying of the mixture obtained at the end of Step 1 or Step 2, followed by the dispersion of the lipidic powder then obtained in a predetermined quantity of water or of an aqueous solution of substances to be encapsulated, in particular the solution obtained in Step 2 bis.

Low-hydration lipidic lamellar phases are thus obtained, or a suspension of liposomes, depending on whether it was selected to disperse the lipidic powder in a small or a large quantity of aqueous medium, as explained in said European document.

The dispersion of hydrated lamellar phases or of the liposomes can thereafter be homogenized, for example according to the process described in document EP-B1-0 107 559.

Optional Step 4

Optionally, the dispersion of the hydrated lipidic lamellar phases or the suspension of liposomes obtained in Step 3-A or Step 3-B above, can be gelled, for example by being mixed with a gel prepared separately, such as a vinyl polymer gel.

Other objects, characteristics and advantages of the invention will be more readily understood on reading the following detailed description given with reference to several examples given by way of illustration and non-restrictively. The percentages given in said examples, are by weight, unless otherwise stated.

EXAMPLE 1

Preparation of a Simple Composition Based on Kola Seed Extracts

The kola seed extracts sold by the Italian company Inverni Della Beffa under the name fluid kola Lipa extract, which have a content in alcaloids expressed as caffeine lower than or equal to 0.5 per thousand, are used as starting materials, hereinafter called kola Lipa.

From such an extract, compositions according to the invention are prepared which have various proportions of kola Lipa, 0.1%, 0.5% and 2%, by dissolving said extract in a phosphate buffer aqueous solution or PBS. After dissolving, the solution obtained is filtered on a filter at 0.8 um in order to remove the insoluble substance.

The compositions according to the invention thus obtained can be used as they are and particularly for the activity tests described hereinafter.

By way of comparison, comparative compositions are also prepared from the product sold by the same Italian company Inverni and called dry kola extract, which has a content of alcaloids expressed as caffeine, equal to about 14%, hereinafter called kola 14.

Said kola 14 is used in the same way to prepare solutions

EXAMPLE 2

Liposomic Composition According to the Invention Containing a Kola Seed Extract Substantially Free of Methylxanthine To this effect, various compositions having different extracts content of 0.1%, 0.5% and 2%, may be prepared in liposomic form, as follows:

Starting with solutions containing kola Lipa in aqueous solution as prepared in Example 1, and adding thereto 1% of lipidic powder obtained according to the spraying method described in document EP-B1-0 087 993, and described briefly in Step 3-B above, and which comprises 9 parts of hydrogenated natural soya lecithin for 1 part of $\beta$-sitosterol.

The lipidic powder is dispersed under magnetic stirring in the aqueous solution until a homogeneous suspension is obtained.

An ultrasonication of these solutions is then carried out, for example with an ultrasonication apparatus called "LABSONIC 1510", for 7 minutes at 200 W and at 4° C., in order to obtain liposomes of size ranging between 100 and 150 nm such as determined on the Nanosizer ® (Coultronic).

With this method, the liposomic compositions obtained contain respectively 0.1%, 0.5% and 2% by weight of kola Lipa, according to the invention, which can be used as they are to constitute cosmetic or dermatological compositions, or in combination with other active agents and/or excipients as will be exemplified hereinafter. Said compositions are also used hereinafter to test their activity.

EXAMPLE 3

Liposomic Composition Containing Total Kola Seed Extracts

The procedure is the same as in Example 2, except that the aqueous solutions used as a basis are those prepared in Example 1-B and containing extract of kola 14 instead of kola Lipa.

The liposomic compositions obtained contain respectively 0.1%, 0.5% and 2% of kola 14. Said compositions can also be used as they are for preparating cosmetic and pharmaceutical, and in particular dermatological, compositions, or they can be completed with other active agents and/or excipients, as described hereinafter. Said compositions are also used on their own for testing their activity.

EXAMPLE 4

Determination of the Lypolytic Activity of the Compositions According to the Invention Evaluation of the Action of the Compositions According to the Invention on the Adipocytes in Culture It was decided to evaluate the efficiency of the compositions according to the invention as lipolytic agents on a line of murine pre adipocytes, such as a 3T3 L1 line available on the market from the company Flow Laboratories, selected for their ability to transform themselves in adipocytes if the culture conditions allow it.

(According to the method of Green, H & Kehinde, C, Cell 1 (1974) 113).

Indeed, this line constitutes a model for study of the adipocyte differentiation in vitro while offering the possibility when the adipocyte phenotype is reached to study the controls of the cellular operation depending on the extra-cellular environment. Said differentiation and its modulation are accompanied by a certain number of morphological and biochemical modifications, the biochemical modifications concerning in particular the release of glycerol.

It is therefore easy to check the lipolytic efficiency of the compounds to be tested by dosing the glycerol released in the culture medium after several days' treatment.

These experiments are carried out as follows:

1) Conditions of Culture

The pre-adipocytes are sown in Petri boxes of 35 mm diameter (20,000 cells per box), in the presence of DMEM ("Dulbecco's Modified Eagle Medium") containing 10% calf's fetal serum and antibiotics (penicillin, streptomycin).

The medium is renewed every 2-3 days.

In these conditions, the culture reaches confluence in one week ($J=J_0$), at this stage, the adipocyte differentiation is activated by the addition of insulin at the concentration of 5 ug/ml of culture medium.

These cells present an over-differentiated state one week after the confluence ($J=J_7$).

2) Treatment—Viability

The cells are treated with the products to be tested at stage $J_7$.

The treatment consists in replacing the culture medium either with a complete medium for the control, or with the same medium containing different concentrations of the product to be tested.

For dosing the released glycerol, the culture medium is recovered between 24 hours and 7 days after the treatment.

The medium with or without the product to be tested is renewed every 2-3 days.

The non-toxicity of the products on the cells in culture is ascertained by determining the rate of total protein according to the Bradford method, described by Mr. M. Bradford (Analytical Biochemistry (1976), 72, 248-54, and which consists in carrying out a maturation with 0.5N sodium hydroxide, and a coloration with Coomassie blue. The extent of the lipolysis is measured by dosage by bioluminescence of the glycerol released in the culture medium.

3) Dosage by Bioluminescence of the Glycerol Released in the Culture Medium

The culture media of the controls or of the treated are collected 2 to 7 days after the treatment.

The supernatants can be stored at $-20°$ C. before dosage.

The glycerol-dosing method is as follows:

The glycerol is dosed by reacting it with ATP in the presence of the glycerolkinase enzyme according to the following reaction:

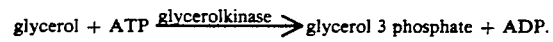

glycerol + ATP $\xrightarrow{\text{glycerolkinase}}$ glycerol 3 phosphate + ADP.

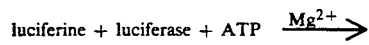

luciferine + luciferase + ATP $\xrightarrow{Mg^{2+}}$ luciferine-luciferase-AMP + pyrophosphate -continued

luciferine-luciferase-AMP $\xrightarrow{O_2}$ oxiluciferine + luciferase + AMP + $CO_2$ + light + emission.

The light emission is picked up by a photomultiplier, such as, for example, a Lumac ® 3M biocounter.

During the mixture of the reagents, the maximum light emission is instantaneous. The dosage proper takes place as follows:

a) Preparation of ATP

A solution of ATP from Sigma's at 50 $\mu$m is prepared in a solution of $MgSO_4$, $7H_2O$ at 0.2 mM.

The ATP is frozen to $-20°$ C. and when used, it will undergo a slow defrosting and will be kept at $0°$ C. (in ice) in darkness.

b) Preparation of Samples

A testing range of glycerol at 0.25, 0.50, 0.75, 1 mM in the buffer citric acid/NaOH 0.1M at a pH of 7.

Dosing of the glycerol contained in the culture medium is carried out after freezing and slow defrosting of the medium. The dilution is chosen so as to arrive between the concentrations of 0.20 and 0.90 nanomoles per ml of reaction volume.

Three tests are conducted on every sample.

c) Dosing Method

In a measuring vessel are placed: 10 $\mu$l of ATP, 50 $\mu$M followed by 20 $\mu$l of preferably purified glycerolkinase available from Boehringer, Mannheim, and 770 $\mu$l of citric acid/NaOH 0.1M buffer of pH 7.

100 $\mu$l of glycerol solution (from the testing range) or of suitably diluted culture medium are then added.

The resulting mixture is stirred strongly for 10 secs.

Then it is incubated for 4 mins. at $20°-22°$ C. in darkness.

100 $\mu$l of luciferine-luciferase (NRB/lumi PM Kit obtainable from Lumac 3M) are injected with the Lumac 3M biocounter pump.

Integration is carried out over 60 secs.

Three tests are conducted for every sample.

d) Mathematical Expression of the Results

Between the emitted light y and the glycerol concentration x, the procedure is a regression procedure according to the method of least squares. There are two criteria for selecting the equation: the determination coefficient $R^2$ and the standard error of the regression (equivalent of the background noise of the experiment).

The polynomial form is what expresses the best the phenomenon. Only the first two degrees give a true information.

What is retained in the equation is only the second degree equation which represents the variation of y of emitted light as a function of the glycerol concentration x of the following form:

$$y = a - bx + cx^2$$

The determination coefficient of the test curve has to be higher than 90% to consider the test range as valid.

The variation coefficient for every one of the concentrations of the test range obtained by bioluminescence is less than 5%.

e) Results

The dosing of glycerol by bioluminescence in the culture medium is tested after 2 days and 7 days of treatment with the extracts of kola 14 and of kola Lipa at a concentration of 1 mg/l in free form as described in Example 1 and in liposomal form as described in Examples 2 and 3.

Three tests are conducted for every sample taken out of three cultures made in the same conditions.

The following results are obtained:

| | RESULTS | | | | |
|---|---|---|---|---|---|
| | Active in free form | | Active in liposomal form | | |
| | control | kola 14% | kola Lipa | Liposome White (control) | Liposome kola 14% | Liposome kola Lipa |
| After 2 days' treatment | | | | | | |
| μmol of glycerol/ml de culture medium | 0.79 | 1.34 | 1.62 | 1.80 | 2.70 | 3.90 |
| | 0.59 | 1.19 | 0.81 | 1.04 | 3.80 | 6.37 |
| | 0.96 | 0.71 | 1.25 | 0.52 | 0.90 | 1.24 |
| average in μmol/ml | 0.78 | 1.08 | 1.23 | 1.12 | 2.46 | 3.83 |
| σ | 0.19 | 0.33 | 0.41 | 0.64 | 1.46 | 2.57 |
| Relative glycerol % | 100 | 138 | 158 | 100 | 220 | 342 |
| After 7 days' treatment | | | | | | |
| μmol of glycerol/ml of culture medium | 1.36 | 1.48 | 1.20 | 1.76 | 3.45 | 4.20 |
| | 0.88 | 1.18 | 1.34 | 1.65 | 4.80 | 5.90 |
| | 0.75 | 0.94 | 1.48 | 0.76 | 4.20 | 4.90 |
| average in μmol/ml | 1.00 | 1.20 | 1.34 | 1.39 | 4.15 | 5.00 |
| σ | 0.32 | 0.27 | 0.14 | 0.55 | 0.68 | 0.85 |
| Relative glycerol % | 100 | 120 | 134 | 100 | 299 | 360 |

It is thus found, completely unexpectedly, that the kola Lipa extracts, which contain substantially no methylxanthines are as active as the kola 14 extract which contain 14% of methylxanthines, whereas the lipolytic activity was, until now, exclusively attributed to the methylxanthines.

It is also found that the kola Lipa extracts even have a lipolytic activity slightly greater than that of the kola 14 extracts.

Finally, the free kola Lipa or kola 14 extracts, meaning extracts not incorporated in liposomes, have a relatively low lipolytic activity, whereas said activity is radically increased in liposomal form, this increase of activity being more significant and complete in the kola Lipa extract containing no methylxanthines, which is totally unexpected, even in relation to the liposomal form.

Various examples of formulations of cosmetic and pharmaceutical compositions, and in particular dermatological compositions, are now described.

EXAMPLE 5

Slimming Cosmetic Cream

A cream is prepared simply by mixing the following components, in the proportions indicated hereunder in grams:

| | |
|---|---|
| Fluid kola Lipa extract | 0.5 g |
| Phosphate buffer | 29.5 g |
| Stabilized W/O emulsion | 70.0 g |
| | 100.0 g |

The cream then obtained is applied once or twice daily on the parts of the body to be treated, by treatments of one to three weeks.

EXAMPLE 6

Slimming Dermatological Gel with Liposomes

A suspension of liposomes is prepared according to Example 2, the extract of fluid kola Lipa being encapsulated. This suspension is then mixed with a neutralized Carbopol 940 ® gel, prepared separately.

The following gelled composition is then obtained:

| | | |
|---|---|---|
| Soya lecithin | | 1.0 g |
| β-sitosterol | | 0.1 g |
| Extract of fluid kola Lipa | | 1.0 g |
| Carbopol 940 ® | | 0.4 g |
| Aqueous excipients stabilized by preserving agents and anti-oxidants | s.q.f. | 100.0 g |

This preparation, when applied daily to the waist, the thighs and the hips, makes it possible to obtain a substantial reduction of the cellulitis in a period of one to three weeks.

EXAMPLE 7

Slimming Emulsion

| Composition: | |
|---|---|
| Soya lecithin | 1.5 g |
| Kola 14 extract | 2.0 g |
| Squalane | 8.5 g |
| Preserving agents | 0.15 g |
| Perfumed and gelled aqueous excipients | 100.0 g |

To obtain this composition, a suspension of liposomes is produced according to the method of Example 3, the extract of kola 14 being encapsulated. Said suspension is thereafter gelled with a Carbopol 940 ® gel neutralized at 1.35%, prepared separately.

The resulting gel is emulsified with a squalane-based oily phase.

The obtained emulsion, which is of pleasant consistency, can be applied daily on the parts of the body to be treated by treatments of two to three weeks.

We claim:

1. A cosmetic or dermatological composition comprising a cosmetically or dermatologically effective amount of an extract of kola seeds substantially free of methylxanthine having a methylxanthine content less than about 0.5 per thousand by weight of the kola seed extract.

2. The composition of claim 1, further comprising a lipidic component selected from the group consisting of hydrated lipidic lamellar phases and liposomes containing said kola seed extracts.

3. The composition of claim 1, wherein the kola seed extract is an extract selected from the group consisting of the kola Nitida plant and the kola Vera Shum plant.

4. The composition of claim 1, wherein the kola seed extract is obtained by an extraction process capable of substantially eliminating the methylxanthine.

5. The composition of claim 1, wherein the kola seed extract substantially free of methylxanthine is obtained from a total kola seed extract from which the methylxanthine is eliminated by a selective solvent.

6. The composition of claim 1, wherein the proportion of the kola seed extract ranges between 0.01 and 10% by weight of the composition.

7. A cosmetic or dermatological composition comprising a lipidic component selected from the group consisting of hydrated lipidic lamellar phases and liposomes containing an extract of kola seeds.

8. The composition of claim 7, wherein the extract of kola seeds is a total extract of kola seeds.

9. The composition of claim 7, wherein the kola seed extract has a methylxanthine content ranging between about 10 and about 14% by weight of the kola seed extract.

10. The composition of claim 7, wherein the kola seed extract is a dry extract.

11. The composition of claim 7, wherein the kola seed plant from which the extract is obtained is selected from the group consisting of the kola Nitida plant and the kola Vera Shum plant.

12. The composition of claim 7, wherein the proportion by weight of the kola seed extract ranges from 0.01 to 10% by weight of the composition.

13. A method of treatment of cellulitis deposits present on body parts, comprising applying to said body parts a cosmetic or dermatological composition comprising a slimming or anti-cellulitis effective amount of an extract of kola seeds substantially free of methylxanthine having a methylxanthine content less than 0.5 per thousand by weight of the kola seed extract.

14. The method of claim 13, further comprising a lipidic component selected from the group consisting of hydrated lipidic lamellar phases and liposomes containing said kola seed extract.

15. The method of claim 13, wherein the proportion by weight of the kola seed extract ranges from 0.01 to 20% by weight of the composition.

16. A method of treatment of cellulitis deposits present on body parts, comprising applying to said body parts a cosmetic or dermatological composition comprising a lipidic component selected from the group consisting of hydrated lipidic lamellar phases and liposomes containing a slimming or anti-cellulitis effective amount of an extract of kola seeds.

17. The method of claim 16, wherein the kola seed extract has a methylxanthine content ranging from 10 to 14% by weight of the kola seed extract.

18. The method of claim 13, wherein the proportion by weight of the kola seed extract ranges from 0.01 to 10% by weight of the composition.

* * * * *